United States Patent [19]

Shutske et al.

[11] 4,337,261

[45] Jun. 29, 1982

[54] (1,2-BENZISOXAZOL)PHENOXYACETIC ACIDS AS DIURETICS

[75] Inventors: Gregory M. Shutske, Somerset; Linda L. Setescak, Somerville; Richard C. Allen, Flemington, all of N.J.

[73] Assignee: Hoechst-Roussel Pharmaceuticals Inc., Somerville, N.J.

[21] Appl. No.: 173,203

[22] Filed: Jul. 28, 1980

[51] Int. Cl.³ .................... A61K 31/42; C07D 261/20
[52] U.S. Cl. .................................... 424/272; 548/241
[58] Field of Search .................... 548/241; 424/272

[56] References Cited

U.S. PATENT DOCUMENTS 3,951,999 4/1976 Saunders et al. .................... 548/241

FOREIGN PATENT DOCUMENTS 744880 7/1970 Belgium .............................. 548/241
48-7633 3/1973 Japan ................................. 548/241

OTHER PUBLICATIONS

Wagner, et al., "Syn. Org. Chem.", J. Wiley & Sons, N.Y. (1953), pp. 226-228, 416-417, 171, 154, 566.

Primary Examiner—Anton H. Sutto
Attorney, Agent, or Firm—Jerome Rosenstock

[57] ABSTRACT

Novel (1,2-benzisoxazol)phenoxyacetic acids and related compounds, methods for preparing same and methods of treatment by administering compositions containing such a compound are described. These compounds are useful as diuretics.

24 Claims, No Drawings

(1,2-BENZISOXAZOL)PHENOXYACETIC ACIDS AS DIURETICS

This invention relates to novel (1,2-benzisoxazol)-phenoxyacetic acids, esters and related compounds which are useful in diuretics, to methods of their preparation, to methods of treatment with pharmaceutically effective amounts thereof and to pharmaceutical compositions containing such a compound as an active ingredient.

To the best of our knowledge, the compounds of the present invention have not been heretofore made, described or suggested. Although 1,2-benzisoxazoloxyacetic acids are known, as reported by Shutske, et al, U.S. patent application Ser. No. 949,128, filed Oct. 6, 1978, now abandoned, neither the instantly described compounds nor their utility are described.

The compounds of this invention can be depicted by the general formula

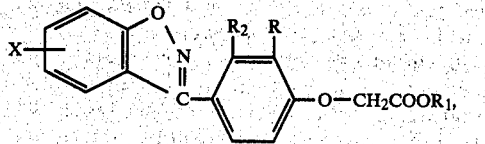

in which $R_2$ in Cl, Br or $CH_3$; R is Cl, Br or $CH_3$; $R_1$ is hydrogen or lower alkyl; and X is hydrogen, halogen, lower alkyl, amino, acylamino or nitro. Also included within the scope of the present invention are the physiologically acceptable salts of the above-depicted compounds.

In the foregoing definitions and throughout this application, the following terms have the following meanings:

"lower" means 1 to 6 carbon atoms;
"halogen" means chlorine, bromine and fluorine.

The physiologically acceptable salts of this invention include those formed with an alkali or alkaline earth metal base or with a non-toxic organic base such as ethanolamine, N-methyl-D-glucamine, etc.

The compounds of the present invention can be prepared by one of the following multi-step sequences of reactions in which unless otherwise indicated R, $R^1$, $R^2$ and X are as previously defined and ambient temperature means about 20°–25° C.

A. A phenol or alkoxybenzene of the formula

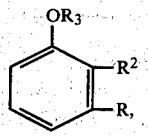

where $R_3$ is hydrogen or lower alkyl, is reacted under Friedel-Crafts conditions with an acid halide of the formula

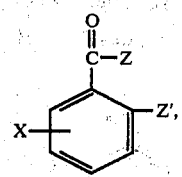

where Z is chlorine or bromine, and Z' is chlorine, fluorine, bromine, hydroxy or alkoxy and X is as defined earlier to provide a compound of the formula

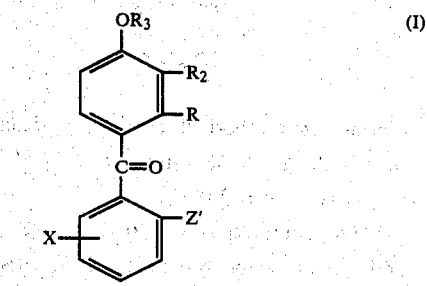

Preferably, 1,2-dichloroethane is used as a solvent and aluminum chloride as the Friedel-Crafts catalyst.

B. The compound I, above, can be dealkylated by any conventional method known in the art to obtain a corresponding compound II in which R is hydrogen,

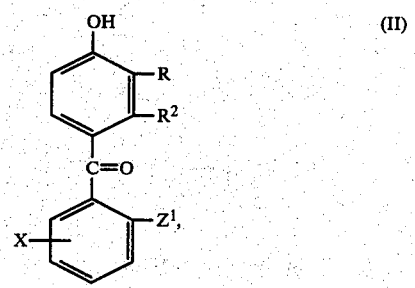

where $Z^1$ is fluorine, chlorine, bromine or hydroxy. Typically, compound I is treated with aluminum chloride in benzene, e.g., at the reflux temperature for about 5 hours.

C. The compound II is treated with hydroxylamine hydrochloride in a suitable solvent, e.g., pyridine, under conventional conditons, e.g., about 48 hours at reflux temperature, to provide the corresponding compound III of the formula

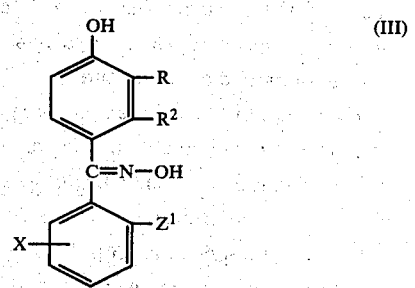

E. When $Z^1$ is fluorine, chlorine or bromine, Compound III is cyclized by treatment with a base, in the presence of a solvent at a temperature of from ambient to reflux of the reaction medium to provide the corresponding bicyclic compound IV of the formula

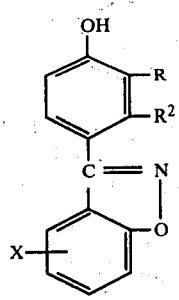

(IV)

A preferred method of cyclizing utilizes the base sodium hydride in the solvent dimethylformamide-benzene mixture at reflux.

F. The compound IV is reacted with a halogenated acetic acid or ester of the formula $ZCH_2CO_2R_1$, where $R_1$ is as earlier defined, to form a compound of the invention

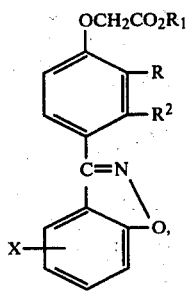

(V)

G. Compound V of the invention, in which $R_1$ is lower alkyl, can be saponified to the corresponding free acid, i.e., where $R_1$ is hydrogen. One method of saponification is carried out with sodium hydroxide in aqueous ethyl alcohol.

H. A compound of the invention prepared in steps F or G above, in which X is nitro is converted by a method known in the art to provide the corresponding compound of the invention in which X is amino. One such method is carried out by treatment with iron filings in an aqueous ethanolic hydrochloride solution.

I. A compound of the invention prepared in step F, G or H above, in which X is amino, is acylated to provide the corresponding compound of the invention in which X is acylamino. One such method involves acylation with acetic anhydride.

J. In an alternative procedure, Compound III, where $Z^1$ is hydroxy, is reacted in a conventional manner with an acid anhydride $(R^1CO)_2O$ or an acid halide $R^1CO$-halogen, where $R^1$ is a lower alkyl, and halogen is fluorine, chlorine or bromine, to form a compound VI

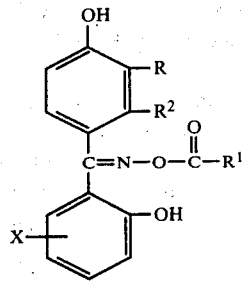

(VI)

K. Compound VI is cyclized by treatment with a base as in Method E. A preferred base is $K_2CO_3$ which is employed to provide the corresponding bicyclic compound IV. Methods F, G, H and I may then be carried out as described above.

All starting materials shown above are either known compounds or are easily prepared by routine methods known to the art from readily available materials.

The compounds of the invention are useful as diuretics due to their ability to produce diuresis in mammals. Such utility is affected when a compound of the invention is administered to a patient requiring appropriate treatment at an oral, parenteral or intravenous dose of from 1–200 mk/kg of body weight per day.

The diuretic activity of the compounds of the subject invention are determined by the diuretic screen test designated as the "Acute Sodium Loaded Mouse" screen. This screen is carried out in the following manner. The acute sodium loaded mouse experiments are performed with groups of male mice weighing 18–24 gms. Drugs are prepared in 1% saline and orally administered in a dosage volume of 10 ml/kg. The animals are housed in metabolic cages, each treatment group consisting of 10 animals, 5 per cage. The tests consist of a vehicle control, a positive control group of 1000 mg/kg urea-treated mice and the potential diuretic agent given at 64 mg/kg.

The resultant pooled urine samples are analyzed for sodium, potassium and chloride. Sodium and potassium values are determined using a flame photometer. Chloride determinations are made by a chloride analyzer. Sodium, potassium and chloride values are expressed as the mean milliequivalents (mEq)/kg/5 hrs. Diuresis is expressed as the mean milliliters (ml)/kg/5 hrs.

Listed below in Table I are the diuretic activities for some of the compounds of this invention.

TABLE I

| Compound | Dose (mg/kg) | Volume (ml/kg/5hrs.) | Na+ (mEq/kg/5hrs.) | K+ | Cl |
|---|---|---|---|---|---|
| Ethyl-4-(1,2-benzisoxazol-3-yl)-2,3-dimethylphenoxyacetate | 64 | 13.8 | 1.1 | 1.4 | 1.5 |
| 4-(1,2-Benzisoxazol-3-yl)-2,3-dichlorophenoxyacetic acid | 64 | 13.2 | 1.5 | 1.5 | 2.1 |
| Control | — | 5.5 | 0.3 | 0.7 | 0.4 |

Compounds of the invention include:
4-(1,2-benzisoxazol-3-yl)-2-chloro-3-methyl-phenoxyacetic acid; 4-(1,2-benzisoxazol-3-yl)-3-chloro-2-methylphenoxyacetic acid; butyl-4-(1,2-benzisoxazol-3-yl)-2,3-dimethylphenoxyacetate; pentyl (4-(1,2-benzisoxazol-3-yl)-2,3-dichlorophenoxyacetate; 4-(6-bromo-1,2-benzisoxazol-3-yl)-2,3-dichlorophenoxyacetic acid; 4-(5-ethyl-1,2-benzisoxazol-3-yl)-2,3- dichlorophenoxyacetic acid; 4-(5-nitro-1,2-benzisoxzaol-3-yl)-2,3-dichlorophenoxyacetic acid; 4-(6-amino-1,2-benzosoxazol-3-yl)-2,3-dichlorophenoxyacetic acid); 4-(5-acetamido-1,2-benzisoxazol-3-yl)-2,3-dichlorophenoxyacetic acid; 4-(5-chloro-1,2-benzisoxazol-3-yl)-2,3-dichlorophenoxyacetic acid;

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

The present invention is further illustrated by the following examples of representative compounds and procedures.

In view of the amendments to the Manual of Patent Examining Procedure, Including Sections 608.01(p); 707.07(l); 2004; 2012 dated January 1981 and received on or about the week of Sept. 14, 1981, Examples 1 to 2E. of the specification are to be read as if they were expressed in the past tense since they are examples which have actually been carried out.

EXAMPLE 1

A. 2'-Fluoro-4-methoxy-2,3-dimethylbenzophenone

Under anhydrous conditions, 2.93 g (0.022 m) of $AlCl_3$ is added gradually over a 30 minute period to a solution of 3.48 g (0.022 m) of $o^3$-fluorobenzoyl chloride in 10 ml of 1,2-dichloroethane. Then 2.72 g (0.02 m) of 2,3-dimethyl anisole in 5 ml of 1,2-dichloroethane is added dropwise. The temperature rises to 35° C. and the mixture is stirred 1 hour after addition. The solvent is evaporated and the residue is treated with 30 ml concentrated HCl and ice. The mixture is extracted with ether, the ether extract is washed with 10% $K_2CO_2$ then washed with $H_2O$, dried ($MgSO_4$) and evaporated to give 4.67 g (92%) of 2-fluoro-4-methoxy-2,3-dimethylbenzophenone. An analytical sample is recrystallized from hexane, m.p. 59°–61° C.

ANALYSIS: Calculated for $C_{16}H_{15}FO_2$: 74.40%C; 5.85%H; 7.36%F. Found: 74.36%C; 5.72%H; 7.54%F.

B. 2'-Fluoro-4-hydroxy-2,3-dimethylbenzophenone

To a solution of 42 g (0.163 m) of 2'-fluoro-4-methoxy-2,3-dimethylbenzophenone of Example 1A in 350 ml of dry benzene, 43.5 g (0.326 m) of $AlCl_3$ is added. The mixture is refluxed 21 hours, poured onto 120 ml concentrated HCl and ice and extracted with ether. The ether extract is washed with water, dried ($Na_2CO_3$) and evaporated to give pure 2'-fluoro-4-hydroxy-2,3-dimethylbenzophenone, 39.4 g (98%). An analytical sample is recrystallized from ethanol/$H_2O$, m.p. 131°–132° C.

ANALYSIS: Calculated for $C_{15}H_{13}FO_2$: 73.76%C; 5.36%H; 7.78%F. Found: 73.72%C; 5.45%H; 7.72%F.

C. 2'-Fluoro-4-hydroxy-2,3-dimethylbenzophenone oxime

A solution of 2 g (0.008 m) of 2'-fluoro-4-hydroxy-2,3-dimethylbenzophenone of Example 1B and 1.5 g (0.02 m) hydroxylamine hydrochloride in 25 ml pyridine is refluxed 16 hours. The pyridine is evaporated in vacuo. The residue is treated with 5% HCl and extracted with $CHCl_3$. The $CHCl_3$ extract is washed with water, dried ($Na_2SO_4$) and evaporated to give 2 g of product. Recrystallization from ethanol/$H_2O$ yields 1 g (50%), m.p. 155°–174° C. of product as a mixture of isomers of 2'-fluoro-4-hydroxy-2,3-dimethylbenzophenone oxime. The purity of this isomeric mixture is demonstrated when a satisfactory analysis is obtained.

ANALYSIS: Calculated for $C_{15}H_{14}FNO_2$: 69.48%C; 5.44%H; 5.40%N. Found: 69.55%C; 5.44%H; 5.41%N.

D. Ethyl 4-(1,2-benzisoxazol-3-yl)-2,3-dimethylphenoxy acetate

To a solution of 5.2 g (0.02 m) of 2'-fluro-4-hydroxy-2,3-dimethylbenzophenone oxime of Example 1C in 50 ml dry DMF and 50 ml dry benzene under $N_2$, 1.2 g (0.005 m) of NaH is added. The mixture is warmed to 50° C. and kept at this temperature for 1½ hours. TLC indicates a new component forms and the absence of starting material. The mixture is cooled to room temperature and a solution of 3.67 g (0.022 m) of ethyl bromoacetate in 10 ml dry dimethylformamide (DMF) is added dropwise. The mixture is stirred ½ hour and water added cautiously to decompose excess NaH. The mixture is extracted with ether, dried ($Na_2SO_4$) and evaporated to give 5.82 g (89%) of ethyl 4-(1,2-benzisoxazol-3-yl)-2,3-dimethylphenoxy acetate. Recrystallization from ethanol/$H_2O$ gives 5 g of pure product, m.p. 87°–88° C.

ANALYSIS: Calculated for $C_{19}H_{19}NO_4$: 70.14%C; 5.86%H; 4.31%N. Found: 70.00%C; 5.92%H; 4.17%N.

E. 4-(1,2-Benzisoxazol-3-yl)-2,3-dimethylphenoxyacetic acid

A solution of 5 g (0.015 m) of ethyl-4-(1,2-benzisoxazol-3-yl)-2,3-dimethylphenoxyacetate of Example 1D, 25 ml 10% NaOH and 25 ml of ethanol is refluxed 3 hours. Ethanol is evaporated in vacuo and 5% HCl is added to the residue until the mixture is acidic. The mixture is extracted with ethyl acetate, dried ($Na_2SO_4$) and evaporated to give 3.8 g (83%) of 4-(1,2-benzisoxazol-3-yl)-2,3-dimethylphenoxyacetic acid, m.p. 146°–152° C. An analytical sample is recrystallized from ethanol/$H_2O$, m.p. 147°–152° C.

ANALYSIS: Calculated for $C_{17}H_{15}NO_4$: 68.67%C; 5.09%H; 4.71%N. Found: 68.50%C; 5.14%H; 4.63%N.

EXAMPLE 2

A. 2'-Fluoro-4-methoxy-2,3-dichlorobenzophenone

To a solution of 3.155 g (0.199 m) of o-fluorobenzoyl chloride in 100 ml 1,2-dichloro ethane 26.54 g (0.199 m) of $AlCl_3$ is added over a 30-minute period. The mixture turns yellow then dark. A solution of 32 g (0.181 m) of 2,3-dichloro anisole in 50 ml of 1,2-dichloroethane is added dropwise. There is an evolution of gas and the temperature rises to 35° C. The mixture is stirred 2 hours and then poured over 100 ml concentrated HCl and 100 ml ice. The organic solvent is evaporated in vacuo and the mixture is extracted with ether. The ether extract is washed with 10% $K_2CO_3$, washed with water, dried ($Na_2SO_4$) and evaporated to give a solid which is recrystallized from ether-hexane giving 38.69 g (70%) of 2'-fluoro-4-methoxy-2,3-dichlorobenzophenone, m.p. 74°–77° C.

ANALYSIS: Calculated for $C_{14}H_9Cl_2FO_2$: 56.21%C; 3.03%H; 6.35%F. Found: 56.20%C; 3.02%H; 6.58%F.

B. 2,3-Dichloro-4-hydroxy-2'-fluorobenzophenone

To a solution of 38.5 g (0.13 m) of 2,3-dichloro-4-methoxy-2'-fluorobenzophenone of Example 2A in 250 ml of dry benzene, 34.67 g (0.26 m) of $AlCl_3$ is added. The mixture is refluxed 5 hours, poured over 100 ml concentrated HCl and 100 ml ice. The mixture is extracted with ethyl acetate, dried ($Na_2SO_4$) and evaporated to give 35 g. Trituration with hexane gives 32.8 g (89%) of 2,3-dichloro-4-hydroxy-2'-fluorobenzophenone. Analytical sample is recrystallized from ether-hexane, m.p. 128°–131° C.

ANALYSIS: Calculated for $C_{13}H_7Cl_2FO_2$: 54.76%C; 2.48%H. Found: 54.87%C; 2.54%H.

C. 2,3-Dichloro-4-hydroxy-2'-fluorobenzophenone oxime

A solution of 31.8 g (0.11 m) of 2,3-dichloro-4-hydroxy-2'-fluorobenzophenone of Example 2B and 15.29 g (0.22 m) of hydroxylamine hydrochloride in 150 ml of pyridine is refluxed 64 hours. The pyridine is evaporated in vacuo, 5% HCl added, extracted with ethyl acetate, dried ($Na_2SO_4$) and evaporated to give 32 g (96%) of 2,3-dichloro-4-hydroxy-2'-fluorobenzophenone oxime. An analytical sample is recrystallized from ethanol/$H_2O$, m.p. 168°–175° C. TLC indicates the product is a mixture of isomers.

ANALYSIS: Calculated for $C_{13}H_8Cl_2FNO_2$: 52.02%C; 2.69%H; 4.67%N. Found: 52.13%C; 2.79%H; 4.70%N.

D. Ethyl 4-(1,2-benzisoxazol-3-yl)-2,3-dichlorophenoxyacetate

To a solution of 18.42 g (0.06 m) of 2,3-dichloro-4-hydroxy-2'-fluorobenzophenone oxime of Example 2C in 120 ml of DMF and 120 ml of benzene 3.6 g (0.15 m) of NaH is added. The mixture is brought to a temperature of 80°–85° C. and held there for 3 hours. The mixture is cooled to room temperature and a solution of 11 g (0.066 m) of ethyl bromoacetate in 20 ml of DMF is added dropwise. After addition the mixture is stirred for ½ hour. Water is added to decompose excess NaH. The mixture is extracted with ethylacetate, dried ($Na_2SO_4$) and evaporated to give 19 g. This is dissolved in toluene and chromatographed on silica gel with toluene as elutant. The product of ethyl 4-(1,2-benzisoxazol-3-yl)-2,3-dichlorophenoxyacetate is isolated from the column, 3.8 g (17%). An analytical sample is recrystallized from 95% ethanol, m.p. 88°–89° C.

ANALYSIS: Calculated for $C_{17}H_{13}Cl_2NO_4$: 55.76%C; 3.58%H; 3.83%N. Found: 55.70%C; 3.50%H; 3.66%N.

E. 4-(1,2-Benzisoxazol-3-yl)-2,3-dichlorophenoxyacetic acid

To a solution of 6.88 g (0.187 m) of ethyl-4-(1,2-benzisoxazol-3-yl)-2,3-dichlorophenoxyacetate of Example 2D in 70 ml of ethanol, 4 ml of 10 N NaOH is added. The mixture is refluxed for 1 hour. The salt which forms is filtered off, and combined with 250 ml of water at 90° C., giving a suspension. Concentrated HCl is added until the mixture is acidic. The mixture is stirred 1 hour at ambient temperature and the product is filtered off. The crude product is recrystallized from ethanol/$H_2O$ and then recrystallized from toluene to give 4.1 g (65%) of pure 4-(1,2-benzisoxazol-3-yl)-2,3-dichlorophenoxyacetic acid, m.p. 166°–167° C.

ANALYSIS: Calculated for $C_{15}H_9Cl_2NO_4$: 53.28%C; 2.68%H; 4.14%N. Found: 53.26%C; 2.73%H; 3.93%N.

We claim:

1. A compound depicted by the formula

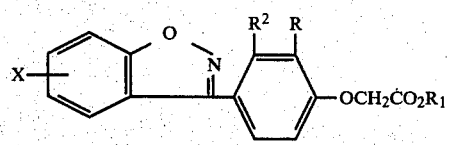

in which R is Cl, CH₃ or Br; R² is Cl, Br or CH₃; R₁ is hydrogen or lower-alkyl; and X is hydrogen, halogen, loweralkyl, amino, acylamino or nitro; and a physiologically acceptable salt thereof.

2. The compound as defined in claim 1 wherein R and R² are CH₃.

3. The compound as defined in claim 1 wherein R and R² are chlorine.

4. The compound as defined in claim 1 wherein R₁ is hydrogen.

5. The compound as defined in claim 1 which is ethyl 4-(1,2-benzisoxazol-3-yl)-2,3-dimethylphenoxyacetate.

6. The compound as defined in claim 1 which is 4-(1,2-benzisoxazol-3-yl)-2,3-dimethylphenoxyacetic acid or a salt thereof.

7. The compound as defined in claim 1 which is ethyl 4-(1,2-benzisoxazole-3-yl)-2,3-dichlorophenoxyacetate.

8. The compound as defined in claim 1 which is 4-(1,2-benzisoxazol-3-yl)-2,3-dichlorophenoxyacetic acid or a salt thereof.

9. A method of producing diuresis which comprises administering to a patient in need of diuresis a diuretically effective amount of a compound depicted by the formula

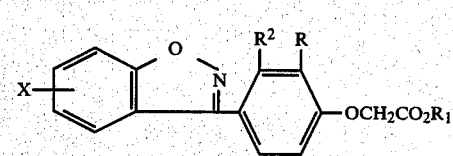

in which R is Cl, CH₃ or Br; R² is Cl, CH₃ or Br; R₁ is hydrogen or lower-alkyl; and X is hydrogen, halogen, loweralkyl, amino, acylamino or nitro; and a physiologically acceptable salt thereof.

10. The method as defined in claim 9 where said compound has R and R² which are CH₃.

11. The method as defined in claim 9 where said compound has R and R² which are chlorine.

12. The method as defined in claim 9 where said compound has R₁ which is hydrogen.

13. The method as defined in claim 9 where said compound is ethyl 4-(1,2-benzisoxazol-3-yl)-2,3-dimethylphenoxyacetate.

14. The method as defined in claim 9 where said compound is 4-(1,2-benzisoxazol-2-yl)-2,3-dimethylphenoxyacetic acid or a salt thereof.

15. The method as defined in claim 9 where said compound is ethyl 4-(1,2-benzisoxazol-3-yl)-2,3-dichlorophenoxyacetate.

16. The method as defined in claim 9 where said compound is 4-(1,2-benzisoxazol-3-yl)-2,3-dichlorophenoxyacetic acid or a salt thereof.

17. A pharmaceutical composition comprising a pharmaceutically effective amount of a compound depicted by the formula

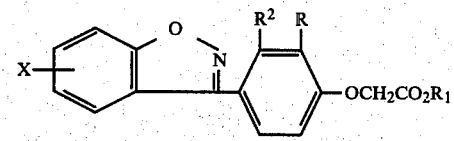

in which R is Cl, Br or CH₃; R₂ is Cl, CH₃ or Br; R₁ is hydrogen or loweralkyl; and X is hydrogen, halogen, loweralkyl, amino, acylamino or nitro; and a physiologically acceptable salt thereof.

18. The pharmaceutical composition defined in claim 17 wherein the R and R² of said compound are CH₃.

19. The pharmaceutical composition defined in claim 17 wherein the R and R² of said compound are chlorine.

20. The pharmaceutical composition defined in claim 17 wherein the R₁ of said compound is hydrogen.

21. The pharmaceutical composition defined in claim 17 which comprises ethyl 4-(1,2-benzisoxazol-3-yl)-2,3-dimethylphenoxyacetate.

22. The pharmaceutical composition defined in claim 17 which comprises 4-(1,2-benzisoxazol-3-yl)-2,3-dimethylphenoxyacetic acid or a salt thereof.

23. The pharmaceutical composition defined in claim 17 which comprises ethyl 4-(1,2-benzisoxazol-3-yl)-2,3-dichlorophenoxyacetate.

24. The pharmaceutical composition defined in claim 17 which comprises 4-(1,2-benzisoxazol-3-yl)-2,3-dichlorophenoxyacetic acid or a salt thereof.

* * * * *

UNITED STATES PATENT AND TRADEMARK OFFICE
CERTIFICATE OF CORRECTION

PATENT NO. : 4,337,261
DATED : June 29, 1982
INVENTOR(S) : Gregory M. Schutske, et al It is certified that error appears in the above-identified patent and that said Letters Patent is hereby corrected as shown below:

Column 4, line 27: "mk/kg" should be --mg/kg--.

Claim 9: "CI" should be --Cl--.

Signed and Sealed this

Twenty-first Day of September 1982

[SEAL]

Attest:

GERALD J. MOSSINGHOFF

Attesting Officer

Commissioner of Patents and Trademarks